United States Patent [19]

Clausen et al.

[11] Patent Number: 4,929,771

[45] Date of Patent: May 29, 1990

[54] PROCESS FOR THE PREPARATION OF ALKYL-SUBSTITUTED PHENOLS OR NAPHTHOLS

[75] Inventors: Martin Clausen; Paul Rys; Wang Junkuan, all of Zurich, Switzerland

[73] Assignee: Ciba-Geigy Corporation, Ardsley, N.Y.

[21] Appl. No.: 278,396

[22] Filed: Dec. 1, 1988

[30] Foreign Application Priority Data

Dec. 9, 1987 [CH] Switzerland .......................... 4800/87

[51] Int. Cl.$^5$ ............................................. C07C 37/08
[52] U.S. Cl. .................................... 568/798; 568/741; 568/768; 568/802
[58] Field of Search ............... 568/573, 741, 798, 802, 568/768

[56] References Cited

U.S. PATENT DOCUMENTS

| 2,796,439 | 6/1957 | Berneis | 568/573 |
| 2,861,107 | 11/1958 | Hiratsuka | 568/573 |
| 4,480,134 | 10/1984 | Fulme | 568/798 |

FOREIGN PATENT DOCUMENTS

| 0288428 | 10/1988 | European Pat. Off. | 568/741 |
| 1093156 | 5/1986 | Japan | 568/573 |
| 641250 | 8/1950 | United Kingdom | 568/573 |

Primary Examiner—Werren B. Lone
Attorney, Agent, or Firm—Kevin T. Mansfield

[57] ABSTRACT

Process for the preparation of alkyl-substituted phenols or naphthols by oxidizing the corresponding dialkylbenzenes or dialkylnaphthalenes, respectively, at elevated temperatures of, for example, 70° to 130° C. by means of oxygen or oxygen donors, in the absence of solvents and in the presence of an alkali metal salt or alkaline earth metal salt of an organic carboxylic acid having 5 to 14 carbon atoms, to give the corresponding 2,6-dialkylnaphthalene-or 1,4-dialkylphenyl monohydroperoxides and subsequently hydrolysing the latter in a customary manner.

The process results in pure, easily isolatable products in a good yield. The products of the process according to the invention are valuable precursors and intermediates for, inter alia, dyes, plastics or pharmaceuticals.

9 Claims, No Drawings

PROCESS FOR THE PREPARATION OF ALKYL-SUBSTITUTED PHENOLS OR NAPHTHOLS

The present invention relates to a novel process for the preparation of alkyl-substituted phenols or naphthols by the oxidation of corresponding dialkylbenzenes or dialkylnaphthalenes and subsequent conventional hydrolysis of the monohydroperoxides formed as intermediates.

The present invention therefore relates to a process for the preparation of compounds of the formula (1) HO - Ar - R, in which Ar is substituted or unsubstituted phenylene or naphthylene and R is $C_1$–$C_5$alkyl, which comprises oxidizing dialkylaryl compounds of the formula (2) $R_1$- Ar - $R_2$ in which $R_1$ and $R_2$ 2 independently of one another are $C_1$–$C_5$alkyl, but are not simultaneously methyl or $C_5$alkyl, and Ar is as defined above in the absence of solvents, at temperatures from 70° to 130° C. by means of oxygen or oxygen donors in the presence of an alkali metal salt or alkal earth metal salt of an organic carboxylic acid having 5 to 14 carbon atoms, to give the corresponding dialkylaryl monohydroperoxides and then hydrolysing the latter in a conventional manner to give the compounds of the formula (1).

The present invention also relates to the compounds of the formula (1), prepared in accordance with the process and to the use thereof as precursors and intermediates for the preparation of, for example, dyes, plastics (polymers) or pharmaceuticals.

The dialkylaryl compounds of the formula (2) which are employed in accordance with the invention are compounds in which $R_1$ and $R_2$ are lower alkyl having 1 to 5 carbon atoms.

The alkyl radicals can be identical or different, but both radicals are not simultaneously methyl or $C_5$alkyl.

Examples of the substitutents $R_1$ and $R_2$ are methyl, ethyl, n-propyl, isopropyl, n-butyl, isobutyl, sec-butyl, tert-butyl and n-pentyl, and also the isomers of the latter.

Preferably, therefore, the compounds of the formula (2) contain a $C_1$–$C_5$-alkyl group and a $C_2$–$C_4$alkyl group as the substituents $R_1$ and $R_2$, and particularly preferred compounds are those in which one of the substituents $R_1$ or $R_2$ is alkyl having 3 or 4 carbon atoms and having a tertiary proton in the α-position relative to the aryl system, for example isopropyl or sec-butyl.

The dialkylaryl compounds of the formula (2) can contain other substituents, for example halogen, preferably chlorine, $C_1$–$C_4$alkyl, $C_1$–$C_4$alakoxy or carboxylic ester (COOR′) (R′=$C_1$–$C_4$alkyl).

Preferred compounds of the formula 2 have the formulae

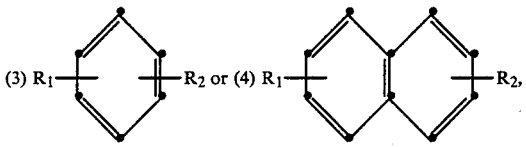

in which $R_1$ and $R_2$ are as defined and the substituents $R_1$ and $R_2$ are preferably located in the 1,4-position in formula (3) and in the 2,6-position in formula (4).

Compounds of the formula (2) which are particularly suitable are, therefore, 2,6-dialkylnaphthalenes or 1,4-dialkylbenzenes, in particular 2-methyl-6-isopropylnaphthalene and 2,6-diisopropylnaphthalene and also 1-methyl-4-isopropylbenzene and 1,4-diisopropylbenzene.

These are known compounds which can be prepared in a known manner, for example by alkylation of the aromatic compounds.

The alkali metal salts or alkaline earth metal salts of organic carboxylic acids having 5 to 14 carbon atoms which are used in the process according to the invention are preferably compounds of the formula

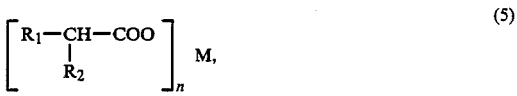

in which $R_1$ is $C_1$–$C_{12}$alkyl and $R_2$ is hydrogen or $C_1$–$C_9$alkyl, the sum of the carbon atoms in the substituents $R_1$ and $R_2$ is 3 to 12, M is lithium, in particular sodium and potassium, and also magnesium, strontium, barium and, especially, calcium and n is 1 or 2, depending on the valency of the metals M.

The following are examples of suitable organic carboxylic acids whose salts can be used: n-valeric acid, caproic acid, n-heptanoic acid, caprilic acid, pelargonic acid, carpic acid, lauric acid, myristic acid, 2-ethylbutyric acid, 4-ethylhexanoic acid or 3-ethylheptanoic acid, and preferably, 2-ethylcaproic acid.

The formation of salts can also take place in situ, i.e. the organic carboxylic acids and, as a rule, alkali metal hydroxides or alkaline earth metal hydroxides are added to the reaction mixture separately.

It is preferable to use the calcium salts and especially the sodium salts of these acids, specifically in amount of 0.1 to 1.0, preferably 0.1 to 0.5, % by weight, relative to the weight of the dialkylaryl compounds of the formula (2).

Optionally, it is preferable to employ additionally so-called reaction initiators for the oxidation reaction according to the invention, for example organic free-radical formers belonging to the group of peroxides, for example di-tert-butyl peroxide, or azo compounds, for example azobisisobutyronitrile. The monohydroperoxides or dihydroperoxides (2,6-diisopropylnaphthalene monohydroperoxide and dihydroperoxide) formed in the oxidation, for example from a previous oxidation, can also be used as so-called reaction initiators.

The amount of these initiators can be about 0.1 to 2.0, preferably 0.1 to 1.0, % by weight and particularly 0.1 to 0.5% by weight, relative to the weight of the dialkylaryl compounds.

The oxidation is carried out in the absence of solvents, i.e., in particular, organic solvents and water. Although small amounts of water can be present in the reaction mixture (an aqueous catalyst), an aqueous reaction medium in the sense of an aqueous solution is not formed thereby.

Molecular oxygen or gases containing oxygen, for example air, or oxygen donors, for example ozone, can be used as the actual oxidizing agent in the process according to the invention.

If oxygen is used as the oxidizing agent, 0.1 to 1 m³, preferably 0.3 to 0.6 m³, for example, of this gas per kg of dialkylaryl compound and per hour is passed through the reaction mixture.

The reaction times are approximately within the range from 1 to 24, preferably 3 to 8 or 3 to 6, hours. The reaction temperatures are within the range from about 70° to 130° C., preferably from about 80° to 120° C. and especially from about 80° to 110° C. It is advantageous to stop the oxidation reaction at a monohydroperoxide content of 20 to 40%, for example 35 to 40%, since after this the oxidation rate can decrease markedly and the formation of by-products and secondary products can increase.

When the oxidation is complete, the reaction mixture can be worked up in various ways. The hydrolysis of the hydroperoxides is carried out in a customary manner, for example by means of concentrated mineral acids; the individual components, for example the intermediates and end products or the unreacted starting materials, can then be isolated, for example by crystallization or extraction.

Working up the reaction mixtures from the oxidation of phenyl compounds, for example of the formula (3), is, as a rule, begun by cooling these mixtures to about 50° to 60° C. and then adding a lower alcohol, in particular methanol. The hydrolysis can then be carried out in a customary manner in this alcoholic (methanolic) solution by adding a concentrated mineral acid, such as sulfuric acid or especially hydrochloric acid, in catalyst amounts (for example 0.5 to 5% by weight, relative to the weight of the solution), while stirring vigorously, and controlling the temperature, and continuing the hydrolysis until hydroperoxides can no longer be detected. The solvent is then removed completely; the residue is taken up in petroleum ether (boiling range 30° to 50° C.) and the resulting solution is extracted with an aqueous alkali metal hydroxide solution, in particular a solution of sodium hydroxide or potassium hydroxide. The unreacted starting materials remain essentially in the organic phase, which, after suitable purification, can be recycled to the oxidation process.

The aqueous phase can optionally be washed with petroleum ether; its pH is then adjusted to a value of about 1 to 2 by adding an acid, in particular a strong mineral acid, such as sulfuric acid or hydrochloric acid, and it is extracted with petroleum ether (30° to 50° C.0.

After the petroleum ether phase has been dried with, for example, potassium bicarbonate or sodium sulfate, the petroleum ether is removed completely by distillation; the alkylphenol is obtained as a crude product which can be recrystallized from petroleum ether (30° to 50° C.). (purity: about 99.0%, analysis by means of high-pressure liquid chromatography - HPLC).

In the case of the reaction mixtures from the oxidation of naphthalene compounds, for example those of the formula (4), when the oxidation reaction is complete, the reaction mixture is cooled to about 50° to 60° C. and a lower alcohol, in particular methanol, is then added. The result of this addition of alcohol is that the temperature of the reaction mixture falls further and, in the course of this, unreacted dialkylaryl compound is precipitated as a finely crystalline precipitate. The bulk of this compound can be crystallized out, and thus removed, by cooling, finally, to about 0° C. The filtrate (the methanolic solution) is then subjected to acid hydrolysis by using, for example, concentrated mineral acids, such as sulfuric acid and especially hydrochloric acid, in catalyst amounts (for example 0.5 to 3% by weight, relative to the weight of the filtrate) and additionally heating the alcoholic (methanolic) solution for a short time (10 to 40 minutes) with stirring at temperatures of 440°0 to 80° C., for example 60° C. The hydrolysis can optionally also be carried out by means of acid solid catalysts, in particular acid ion exchangers.

The alcohol (methanol) is then removed, and a nonpolar solvent (for example hexane, heptane or petroleum ether) is added to the residue and the mixture iswarmed to approx. 60° C. The insoluble fraction is then isolated, washed with an inert solvent (petroleum ether) and finally dried. This product is the dihydroxynaphthyl compound, which is obtained in a very good state of purity.

When the filtrate obtained after the removal of this dihydroxyaryl compound is cooled, the alkyl-substituted naphthol crystallizes out and is also isolated and dried (purity: about 98%, HPLC).

If necessary, this compound can be purified further by recrystallization from petroleum ether or hexane.

The advantages of the process according to the invention are firstly the avoidance of heavy metal catalysts, and secondly the higher reaction temperatures and hence shorter reaction times which can be achieved without the presence of organic solvents and water as a reaction medium, and, finally, also the easy separation of the alkyl-substituted phenols or naphthols obtained in accordance with the invention from the dialkylaryl compounds employed as the starting compound (for example the dialkylnaphthalene compounds are precipitated when the reaction mixture is taken up in, for example, methanol), and also from the monohydroperoxides and dihydroperoxides of the said starting compounds, which are formed as intermediates.

The products according to the process are obtained in a good yield and purity. They are suitable precursors and intermediates for the preparation of, for example, dyes, polymers, synthetic fibres or pharmaceuticas.

The examples below illustrate the process according to the invention, but without limiting it to these examples. Parts and percentages are by weight, unless stated otherwise. The temperature is indicated in degrees Centigrade.

EXAMPLE 1

10 g of 2,6-diisopropylnaphthalene (purity determined by analysis by gas chromatography (GC) 97%) are heated to 100° C. in a 100 ml four-necked flask equipped with a stirrer, a thermometer, a reflux condenser and a gas inlet frit. 0.1 g of a solution (catalyst mixture) composed of 4 parts of 2-ethylcaproic acid, 2 parts of sodium hydroxide and 5 parts of water, followed by 0.1 g of di-tert-butyl peroxide, are added with vigorous stirring, and the supply of oxygen from a pressure cylinder at a rate of 80 ml/min is started. The supply of xoygen and heat is stopped after 3 hours. Analysis of the reaction product by means of HPLC indicates, besides unchanged starting material (2,6-diisopropylnaphthalene), oxidation products consisting, to the extent of 91%, of the corresponding hydroperoxides (2,6-diisopropylnaphthalene monohydroperixide and 2,6-diisopropylnaphthalene dihydroperoxide). The ratio by weight of monohydroperoxide to dihydroperoxide is 9:1. The reaction product is then cooled to about 660° C. and 40 g of methanol are then added. 1 ml of concentrated hydrochloric acid is added dropwise to the methanolic solution, with temperature control and vigorous stirring. The mixture is stirred for 30 minutse at 60° C. After this time no further peroxides are detected in the reaction product. The bulk of the unreacted 2,6-diisopropylnaphthalene crystallizes by cooling the solution to approx. 4° C., and can be removed. Drying under a high vacuum gives 4.7 g of 2,6-diisopropylnaphthalene (purity: 98%, HPLC).

Methanol is removed from the residual solution. 200 g of n-hexane are added to the residue, and the remaining mixture of solvent and product is warmed to 60° C. The undissolved fractions of this mixture are removed, washed with hexane and petroleum ether (110° to 140° C.) and dried. 0.21 g of 2,6-dihydroxynaphthalene are obtained (purity: 97%, HPLC).

Flocculent, voluminous 6-hydroxy-2-isopropylnaphthalene crystallizes when the filtrate obtained after the removal of the 2,6-dihydroxynaphthaline is cooled to approx. 4° C. After isolation and drying, 2.35 g are obtained (purity: 99%, HPLC).

A further fraction (0.2 g) is obtained in the same manner after the filtrate has been concentrated. The yield of 6-hydroxy-2-isopropylnaphthalene, relative to the monohydroperoxide, is 90%. The melting point of the compound is 110 C.

2-Methyl-6-isopropylnaphthalene can also be oxidized to 6-hydroxy-2-methylnaphthalene analogously.

Instead of the catalyst mixture mentioned it is also possible to use an aqueous mixture containing sodium hydroxide or potassium hydroxide and one of the following carboxylic acids: n-valeric acid, caproic acid, n-heptanoic acid, caprylic acid, pelargonic acid, capric acid, lauric acid, myristic acid, 2-ethylbutyric acid, 4-ethylhexanoic acid or 3-ethylhpetanoic acid.

EXAMPLE 2

10 g of 2,6-diisopropylnaphthalene are oxidized as described in Example 1, except for the reaction temperature, which is adjusted to 110° C. The oxygen and the heating are switched off after 3 hours. Analysis of the reaction product by HPLC indicates, besides unchanged starting material (2,6-diisopropylnaphthaline), oxidation products consisting to the extent of 85% of the corresponding 2,6-diisopropylnaphthalene monohydroxide and dihydroxide. The ratio by weight of monohydroperoxide to dihydroperoxide is 5.4:1.

The desired end product—6-hydroxy-2-isopropylnaphthalene - is worked up and isolated by removing unreacted starting material and 2,6-dihydroxynaphthalene as indicated in Example 1. The yield of 6-hydroxy-2-isopropylnaphthalene, relative to the monohydroperoxide, is 92%.

EXAMPLE 3

15 g of 1,4-diisopropylbenzene (purity determined by analysis by gas chromatography (GC) 98%) are heated to 80° C. in a 100 ml four-necked flask equipped with a stirrer, a thermometer, a reflux condenser and a gas inlet frit. 0.2 g of a solution (catalyst mixture) composed of 4 parts of 2-ethylcaproic acid, 2 parts of sodium hydroxide and 5 parts of water, followed by 0.02 g of azobisisobutyronenitrile, is added with vigorous stirring, and the supply of oxygen from a pressure cylinder is started at a rate of 80 ml/min. The supply of oxygen and heat is stopped after 6 hours.

Analysis of the reaction product by means of HPLC indicates, besides unchanged starting material, oxidation products consisting to the extent of 90% of the corresponding hydroperoxides (1,4-diisopropylbenzene monohydroperoxide and 1,4-diisopropylbenzene dihydroperoxide). The ratio by weight of monohydroperoxide to dihydroperoxide is 10:1.

The reaction product is then cooled to about 60° C. and 40 g of methanol are added. 1 ml of concentrated hydrochloric acid is added dropwise to the methanolic solution with temperature control and vigorous stirring. The mixture is stirred for 30 minutes at 60° C. After this time no further peroxides are detected in the reaction channel. The methanol is then removed from the solution. 40 g of petroleum ether (boiling range 30° to 50° C.) is then added to the reaction mixture, and the resulting solution is extracted with twice 30 g of an aqueous alkali of pH 10 to 11. When the combined aqueous extracts have been washed with 30 g of petroluem ether (30° to 50° C.), the pH is adjusted to a value of 1 to 2 by adding hydrochloric acid, and the mixture is extracted with 30 g of petroleum ether (30° to 50° c.). The organic phase is dried over sodium sulfate and the solvent is then removed completely.

2.35 g of 4-isopropylphenol are obtained, which corresponds to a yield of 95% relative to the monohydroxperoxide (purity 99%, HPLC). The crude product can be recrystallized from petroleum ether (30° to 50° C.). The melting point is 62.7° C.

1,4-Diisopropylbenzene can be recovered from the organic phase after extraction with alkali and can be recycled to the oxidation process after suitable purification.

1-Methyl-4-isopropylbenzene can also be oxidized to p-cresol analogously.

Instead of the catalyst mixture mentioned, it is also possible to use an aqueous mixture containing sodium hydroxide or potassium hydroxide and one of the following carboxylic acids: n-valeric acid, caproic acid, n-heptanoic acid, caprylic acid, pelargonic acid, carpic acid, lauric acid, myristic acid, 2-ethylbutyric acid, 4-ethylhexanoic acid or 3-ethylheptanoic acid.

What is claimed is:

1. A process for the preparation of compounds of the formula (1) HO - Ar - R, in which Ar is substituted or unsubstituted phenylene or naphthalene and R is $C_1$–$C_5$alkyl, which comprises oxidizing dialkylaryl compounds of the formula in which $R_1$ and $R_2$ independently of one another are $C_1$–$C_5$alkyl, but are not simultaneously methyl or $C_5$alkyl, and Ar is as defined above in the absence of solvents, at temperatures from 70° to 130° C. by means of oxygen or oxygen donors in the presence of an alkali metal salt or alkaline earth metal salt of an organic carboxylic acid having 5 to 14 carbon atoms, to give the corresponding dialkylaryl monohydroperoxides and then hydrolysing the latter under acidic conditions to give the compounds of the formula (1).

2. A process according to claim 1, wherein the oxidation is carried out in the absence of organic solvents at temperatures from 70° to 130° C. by means of oxygen or oxygen donors in the presence of an alkali meatl salt or alkaline earth metal salt of an organic carboxylic acid having 5 to 14 carbon atoms.

3. A process according to claim 1, wherein said dialkylaryl compounds of the formula (2) are 2,6-dialkylnaphthalenes or 1,4-dialkyl-benzenes whose alkyl substituents $R_1$ and $R_2$ are as defined in claim 1.

4. A process according to claim 3, wherein said dialkylaryl compounds of the formula (2) contain, as alkyl substituents $R_1$ and $R_2$, $C_1$–$C_5$alkyl, one of the substituents $R_1$ or $R_2$ being $C_3$ alkyl or $C_4$ alkyl having a tertiary proton in the α-position relative to the aryl system.

5. A process according to claim 4, wherein said dialkylaryl compounds of the formula (2) are 2-methyl-6-isopropylnaphthalene, 2,6-diisopropylnaphthalene, 1-methyl-4-isopropylbenzene or 1,4-diisopropylbenzene.

6. A process according to claim 1, wherein the alkali metal salts of alkaline earth metal salts of the organic carboxylic acids have the formula

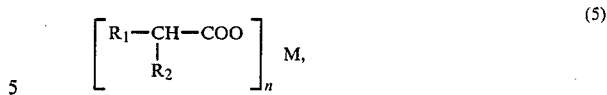

in which $R_1$ is $C_1$–$C_{12}$alkyl and $R_2$ is hydrogen or $C_1$–$C_9$alkyl, the sum of the carbon atoms in the substituents $R_1$ and $R_2$ is 3 to 12, M is lithium, sodium, potassium, magnesium, strontium, barium or calcium, and n is 1 or 2, depending on the valency of the metals M.

7. A process according to claim 6, wherein the amount of the alkaline earth metal or of the alkali metal salts of the organic carboxylic acids is 0.1 to 1.0% by weight, relative to the weight of the dialkylaryl compounds of the formula (1).

8. A process according to claim 7, wherein the amount of the salts of the organic carboxylic acids is 0.1 to 0.5% by weight, relative to the weight of the dialkylaryl compounds of the formula (2).

9. A process according to claim 7, wherein the oxidation is carried out at temperatures from 80° to 120° C.

* * * * *

UNITED STATES PATENT AND TRADEMARK OFFICE
CERTIFICATE OF CORRECTION

PATENT NO. : 4,929,771

DATED : 5/29/90

INVENTOR(S) : Clausen et al.

It is certified that error appears in the above-identified patent and that said Letters Patent is hereby corrected as shown below:

COLUMN 6:

In claim 1 of the printed patent specification, formula (2) should be inserted into the space after line 6. Line 7 should read:

(2) $R_1-Ar-R_2$

Signed and Sealed this

Fourteenth Day of July, 1992

Attest:

DOUGLAS B. COMER

Attesting Officer

Acting Commissioner of Patents and Trademarks